United States Patent
Maltbie et al.

(10) Patent No.: US 9,244,022 B2
(45) Date of Patent: Jan. 26, 2016

(54) MANNEQUINS FOR USE IN IMAGING AND SYSTEMS INCLUDING THE SAME

(75) Inventors: David John Maltbie, Hamilton, OH (US); Richard Tweddell, III, Liberty Township, OH (US); Darren Paul Trokhan, Hamilton, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 1259 days.

(21) Appl. No.: 13/161,722

(22) Filed: Jun. 16, 2011

(65) Prior Publication Data
US 2012/0321040 A1    Dec. 20, 2012

(51) Int. Cl.
| | |
|---|---|
| *G01N 23/04* | (2006.01) |
| *G09B 23/30* | (2006.01) |
| *G09B 23/28* | (2006.01) |
| *A61B 6/12* | (2006.01) |
| *A61F 13/84* | (2006.01) |
| *G01N 21/47* | (2006.01) |

(52) U.S. Cl.
CPC .............. *G01N 23/04* (2013.01); *G09B 23/286* (2013.01); *G09B 23/30* (2013.01); *A61B 6/12* (2013.01); *A61F 2013/8488* (2013.01); *G01N 21/4785* (2013.01); *G01N 2223/3035* (2013.01); *G01N 2223/419* (2013.01); *G01N 2223/634* (2013.01)

(58) Field of Classification Search
CPC ...................................................... A61B 6/583
USPC ............................................................ 378/18
See application file for complete search history.

(56) References Cited

U.S. PATENT DOCUMENTS

| | | | |
|---|---|---|---|
| 5,419,729 | A | 5/1995 | Gross |
| 6,839,402 | B2 | 1/2005 | Stabe et al. |
| 6,904,820 | B2 | 6/2005 | Tate et al. |
| 6,931,951 | B2 | 8/2005 | Wright et al. |
| 7,174,774 | B2 | 2/2007 | Pawar et al. |
| 7,549,866 | B2 | 6/2009 | Cohen et al. |
| 7,663,648 | B1 | 2/2010 | Saldanha et al. |

(Continued)

FOREIGN PATENT DOCUMENTS

| | | |
|---|---|---|
| EP | 1595465 B1 | 11/2005 |
| EP | 2224362 A1 | 9/2010 |

(Continued)

OTHER PUBLICATIONS

T.J. Heindel et al., "An X-ray system for visualizing fluid flows", Flow Measurement and Instrumentation 19 (2008), pp. 67-78.

(Continued)

*Primary Examiner* — Hoon Song
(74) *Attorney, Agent, or Firm* — Andres E. Velarde; Andrew A. Paul

(57) ABSTRACT

A mannequin may include a skin layer, an axis of rotation and a photon transmissive filler. The skin layer may include a contoured surface. The skin layer may have a thickness of less than about 10 mm. The contoured surface may be formed into a three-dimensional shape that substantially matches anatomy of a person or a statistical model representing a group of people. The axis of rotation may intersect the mannequin and may define a center for collection of X-ray images along a substantially circular path. The photon transmissive filler may be at least partially surrounded by the skin layer. The photon transmissive filler may have a an average specific gravity of less than about 0.5 g/cc.

50 Claims, 4 Drawing Sheets

(56) References Cited

U.S. PATENT DOCUMENTS

| | | |
|---|---|---|
| 7,712,640 B2 | 5/2010 | Honer et al. |
| 2005/0197564 A1* | 9/2005 | Dempsey ................. 600/411 |
| 2007/0048709 A1 | 3/2007 | Ales, III et al. |
| 2007/0140413 A1* | 6/2007 | Saracen ..................... 378/18 |
| 2008/0004833 A1 | 1/2008 | Becker |
| 2008/0034849 A1* | 2/2008 | Honkonen et al. ............. 73/73 |
| 2008/0049899 A1 | 2/2008 | Rothschild |
| 2008/0197158 A1* | 8/2008 | Tu ............................. 223/66 |
| 2008/0253525 A1 | 10/2008 | Boyden et al. |
| 2009/0099588 A1* | 4/2009 | Makower et al. ........... 606/191 |
| 2010/0116036 A1 | 5/2010 | Honkonen et al. |

FOREIGN PATENT DOCUMENTS

| | | |
|---|---|---|
| JP | 2003-067725 A | 3/2003 |
| WO | WO 96/12459 A2 | 5/1996 |
| WO | WO 2005/088484 A1 | 9/2005 |
| WO | WO 2007/146152 A2 | 12/2007 |
| WO | WO 2009/026492 | 2/2009 |

OTHER PUBLICATIONS

S.Siegfried, et al., NMR Imaging in Chemical Engineering (2006), Hardware and Methods, pp. 47-76.

S.Siegfried, et al., NMR Imaging in Chemical Engineering (2006), Fluids and Flows, pp. 359-382.

S.Siegfried, et al., NMR Imaging in Chemical Engineering (2006), NMR for Food Quality Control, pp. 471-489.

J.M. Wells, "On Non-Destructive Evaluation Techniques for Ballistic Impact Damage in Armor Ceramics", pp. 238-248.

* cited by examiner

MANNEQUINS FOR USE IN IMAGING AND SYSTEMS INCLUDING THE SAME

FIELD OF THE INVENTION

The present specification generally relates to human analog devices and systems including the same and, more specifically, mannequins suitable for use in imaging and systems including the same.

BACKGROUND OF THE INVENTION

Observing and/or analyzing the interior of various consumer products can provide useful or important information to the product's manufacturer or others. For example, the manufacturer may want to observe the interior of the product, e.g. an absorbent article and its constituents or components or that of its packaging in an actual or simulated use conditions. The interior of absorbent articles may be observed using techniques for obtaining data, such as imaging or scanning techniques such as, for example, MRI, X-ray, computed tomography (CT) imaging (e.g., two-dimensional CT and/or three-dimensional CT).

In the case of X-ray and/or CT imaging, a human analog device may be utilized to "wear" the absorbent article and simulate usage, i.e., transmit a fluid from the analog device into the absorbent article. However, many of the human analog devices such as, for example, toy dolls, are too dense in near the perineum area for CT imaging. Moreover, the human analog devices may comprise non continuous skin and may be not properly scaled to a human. Such devices may cause fluid to flow in unrealistic patterns and ineffectively simulate the wearing of the absorbent article. Additionally, it is noted that human analog devices such as, for example, clothing display mannequins, are generally not intended to accurately simulate human dimensions in unexposed regions or regions intended to be covered by clothing (e.g., clothing display mannequins are generally anatomically inaccurate). Furthermore, clothing display mannequins are generally not capable of transmitting body exudates into an absorbent article. Accordingly, a need exists for alternative mannequins for evaluating absorbent articles and systems including the same.

SUMMARY OF THE INVENTION

In one example, a mannequin may include a skin layer, an axis of rotation and a photon transmissive filler. The skin layer may include a contoured surface. The skin layer may have a thickness of less than or equal to about 10 mm. The contoured surface may be formed into a three-dimensional shape that substantially matches the anatomy of a person or a statistical model representing a group of people, or an engineered hypothetical person. The axis of rotation may intersect the mannequin and may define a center for collection of X-ray images along a substantially circular path. The photon transmissive filler may be at least partially surrounded by the skin layer. The photon transmissive filler may have an average specific gravity of less than or equal to about 0.5 g/cc.

In another example, a mannequin may comprise a contoured surface and a photon transmissive filler. The contoured surface may be formed into a three-dimensional shape. The three-dimensional shape may match anatomy of a person or a statistical model representing a group of people, or an engineered hypothetical person. The photon transmissive filler may be at least partially surrounded by the contoured surface. More than about 50% of a mannequin image within a region of interest of a test image of the mannequin has a transmissive parameter value greater than about 10%.

In yet another example, a system for collecting X-ray images may include a photon source, a photon detector, a mannequin, a mannequin fixture, and a controller. Photons may be transmitted from the photon source to the photon detector along a transmission path. The mannequin may include a contoured surface. The contoured surface may be formed into a three-dimensional shape that substantially matches anatomy of a person or a statistical model representing a group of people or an engineered hypothetical person. The mannequin may be placed along the transmission path wherein the photons are transmitted through an imaged portion of the contoured surface. The mannequin fixture may be coupled to the mannequin. The imaged portion of the contoured surface may be spaced at least an artifact distance away from the mannequin fixture. The controller may cause the photon detector to collect X-ray projections as relative rotational motion occurs between the mannequin and the photon detector.

For any of the examples, the mannequin may be suitable for use with imaging or scanning techniques such as, for example, MRI, X-ray, computed tomography (CT) imaging (e.g., two-dimensional CT and/or three-dimensional CT), and may be referred to as an MRI mannequin, an X-ray mannequin, and/or a CT mannequin, accordingly. Further description of how such mannequins may be used with such imaging or scanning techniques is set forth below.

These and additional features provided by the examples described herein will be more fully understood in view of the following detailed description, in conjunction with the drawings.

BRIEF DESCRIPTION OF THE DRAWINGS

The drawings are illustrative in nature and not intended to limit the subject matter defined by the claims. The following detailed description can be understood when read in conjunction with the following drawings, where like structure is indicated with like reference numerals and in which:

DETAILED DESCRIPTION OF THE INVENTION

Figure 1:
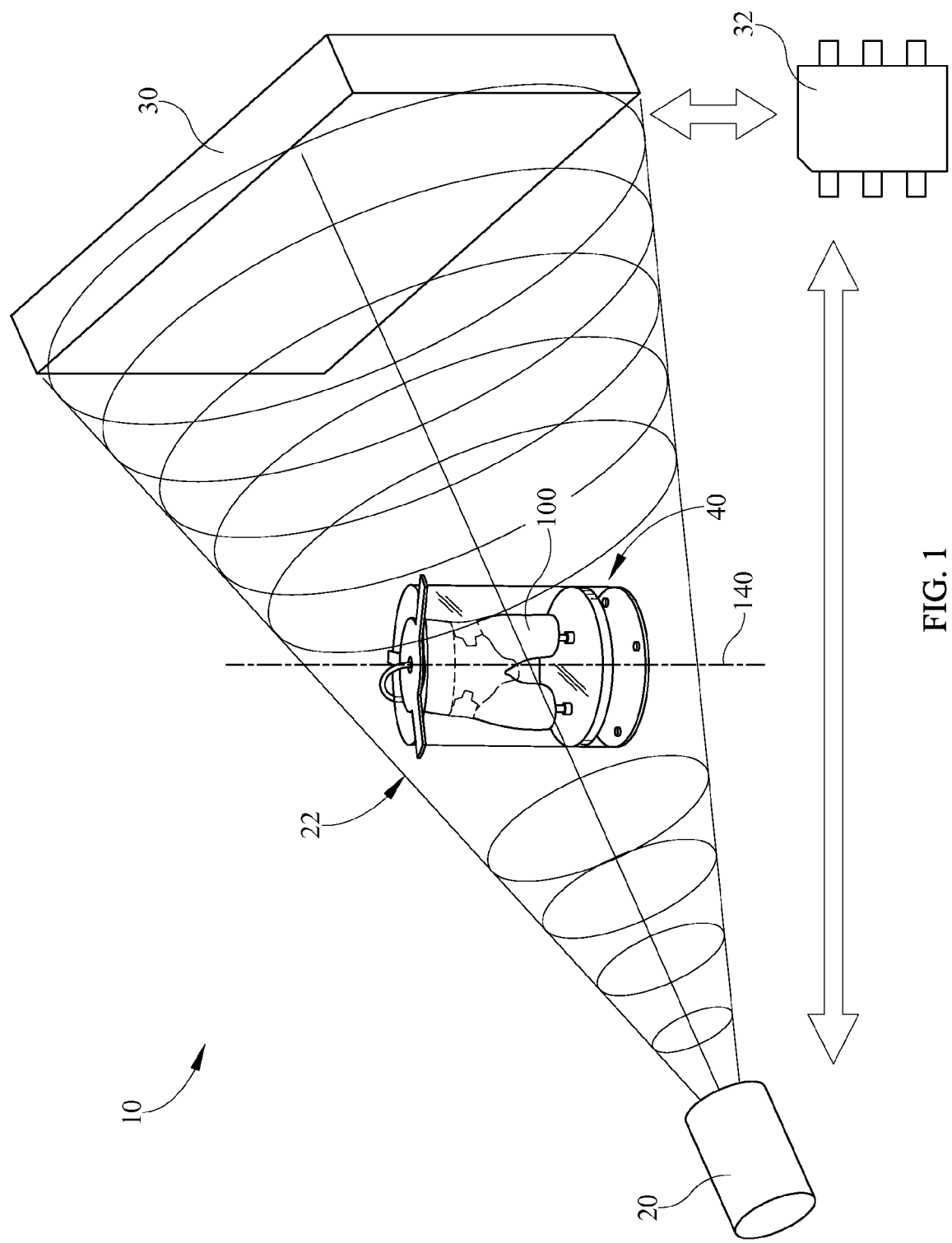
FIG. 1 depicts a system for collecting computed tomography images according to one or more examples shown and described herein.

As used herein with the various illustrated examples described below, the following terms include, but are not limited to, the following meanings.

"Absorbent article" refers to devices that absorb and/or contain body exudates, and, more specifically, refers to devices that can be placed against and/or in proximity to the body of the wearer to absorb and contain the various exudates discharged from the body. As used herein, the term "body fluids" or "body exudates" includes, but is not limited to, urine, blood, vaginal discharges, breast milk, sweat and fecal matter. Absorbent articles may include bath tissue, paper towels, wipes (e.g., disinfectant, cleansing, facial, hand, baby, perineal) diapers, training pants, adult incontinence under-garments, wound care dressings, catamenial products, feminine hygiene products, such as pads or tampons, breast pads, care mats, bibs, wound dressing products, and the like.

"Controller" refers to a computing device capable of executing machine readable instructions such as an integrated circuit, a microchip, a computer, and the like. It is noted that the examples described herein may comprise distributed computing devices. Specifically, multiple autonomous controllers may be communicably coupled and configured to cooperate in a manner analogous to the single controller.

"Communicably coupled" refers to an exchange of data via a communication medium such as for example, electrical transmission over a conductive medium, electromagnetic transmissions over the air, optical transmissions over a waveguide, and the like.

"Grey value" refers to a relative amount of X-ray radiation (i.e., projections) absorbed and/or detected by an X-ray detector. Furthermore, it is noted that grey value data may be scaled to any scale and/or data units such as, for example, 8 bit, 12 bit, 16 bit, and/or 32 bit data that may be indicative of the intensity of the X-ray projections detected by an X-ray detector.

"Coupled" means that multiple objects are united together such as for example, bolted, welded, anchored, integral, and the like. "Coupled" may mean that the respective objects are directly joined together or the respective objects may be joined together by one or more components there between.

"Interior" refers to any portion of a product or packaging that is not readily visible to the naked eye viewing the exterior of the product or packaging. In some examples, the interior of a product or packaging may include one or more of internal surfaces and internal components of the product or packaging. In some examples, the interior may either include or exclude liquids, semi-solids, solids, emulsions, and colloids introduced into the product or packaging that may or may not interact with the product or packaging, but do not form an integral part of the product or packaging. Non-limiting examples would be urine or feces (actual or synthetic) introduced into a diaper.

"Disposable" is used in its ordinary sense to mean an article that is disposed or discarded after a limited number of usage events over varying lengths of time, for example, less than about 20 events, less than about 10 events, less than about 5 events, or less than about 2 events.

"Diaper" refers to an absorbent article generally worn by infants and incontinent persons about the lower torso so as to encircle the waist and legs of the wearer and that is specifically adapted to receive and contain urinary and fecal waste. As used herein, term "diaper" also includes "pants" which is defined below.

"Substantial" and forms thereof, as used herein, means of ample or considerable proportion such as about 80% or more, preferably about 85% or more, more preferably about 90% or more, such as, for example, about 95% or more, about 98% or more or about 99% or more.

"Pant" or "training pant," as used herein, refer to disposable garments having a waist opening and leg openings designed for infant or adult wearers. A pant may be placed in position on the wearer by inserting the wearer's legs into the leg openings and sliding the pant into position about a wearer's lower torso. A pant may be pre-formed by any suitable technique including, but not limited to, joining together portions of the article using refastenable and/or non-refastenable bonds (e.g., seam, weld, adhesive, cohesive bond, fastener, etc.). A pant may be preformed anywhere along the circumference of the article (e.g., side fastened, front waist fastened). While the terms "pant" or "pants" are used herein, pants are also commonly referred to as "closed diapers," "prefastened diapers," "pull-on diapers," "training pants," and "diaper-pants." Suitable pants are disclosed in U.S. Pat. No. 5,246,433, issued to Hasse, et al. on Sep. 21, 1993; U.S. Pat. No. 5,569,234, issued to Buell et al. on Oct. 29, 1996; U.S. Pat. No. 6,120,487, issued to Ashton on Sep. 19, 2000; U.S. Pat. No. 6,120,489, issued to Johnson et al. on Sep. 19, 2000; U.S. Pat. No. 4,940,464, issued to Van Gompel et al. on Jul. 10, 1990; U.S. Pat. No. 5,092,861, issued to Nomura et al. on Mar. 3, 1992; U.S. Patent Publication No. 2003/0233082 A1, entitled "Highly Flexible And Low Deformation Fastening Device", filed on Jun. 13, 2002; U.S. Pat. No. 5,897,545, issued to Kline et al. on Apr. 27, 1999; U.S. Pat. No. 5,957,908, issued to Kline et al on Sep. 28, 1999.

It may be desirable to observe the interior of various products in actual or simulated usage conditions. For purposes of illustration only, one example of a product category whose interior may be of interest during use conditions is absorbent articles, preferably disposable absorbent articles. It also may be desirable to observe the interior of many other products and their packaging during use and other conditions. With regard to the example of absorbent articles, illustrative absorbent articles include diapers, incontinence pads, training pants, tampons, catamenial napkins, paper towels, etc. Some of these examples include an absorbent core that may receive and hold bodily exudates and/or a sealing member that mitigates the flow of exudates between the absorbent article and a wearer of the absorbent article. Any absorbent article with any suitable absorbent core or sealing member may be evaluated with the examples described herein.

A performance characteristic of absorbent articles that may be of interest is the product's ability to absorb and contain bodily discharges, including initial, subsequent, and continuous or repeated discharges, and the product's ability to contain such discharges without leaking. If the product does leak, it may be of interest to know where and how much it leaks. Another characteristic of absorbent articles that may be of interest to a manufacturer is the actual, as opposed to predicted, flow pattern of liquids as they move through the absorbent article after contacting the absorbent article. The flow path of liquids within the interior of the absorbent article may provide useful information, including but not limited to where the absorbent core should have increased absorptive capacity, how to channel liquids away from areas that may be more susceptible to leakage, how to wick and otherwise control fluid flow, etc., where a given region of an article is more susceptible to leakage, information regarding the actual flow path, including direction, timing, etc., of the liquid to the region in question may aid in improving the product's ability to contain bodily discharges.

In general, one reason why an absorbent article may be unable to adequately handle multiple discharges of liquid is the article's limitations regarding transporting discharged liquid away from the region of discharge, once the absorbent capacity of that region has been reached. Thus, the overall performance of the absorbent article may be affected by the article's properties with respect to transporting liquids to the various regions of the absorbent core, including regions that may be located away from the area where the discharged liquids first contact the absorbent core. Other properties relating to the interior of an absorbent article also may be of interest to a manufacturer. For example, information regarding how quickly various absorbent core materials absorb liquids, and how they then transport those liquids, may be helpful in product design and other contexts. In addition, information regarding actual fit—such as how the interior of the article actually contacts and contours the various body configurations—may be helpful in product design, manufacturing, marketing, and other contexts. Indeed, product fit may be of increased importance to various types of products, and to various types of absorbent articles, when compared to others. It may be of interest to determine the area(s) and amount of less than desirable fit.

X-ray and/or computed tomography (CT) imaging (e.g., two-dimensional CT and/or three-dimensional CT) may be utilized to obtain data indicative of the performance characteristics of an absorbent article. Generally, a CT scan produces images of an object by collecting raw data indicative of X-ray projections (i.e., photons) that have been transmitted through the object and reconstructing the images into an image of the object. The object may be positioned between an X-ray detector and an X-ray source such that X-ray projections emitted by the X-ray source impinge upon the object and the X-ray detector. The final data set may be made more dimensionally complex than the X-ray detector by reconstructing a plurality of raw data sets collected by the X-ray detector. Specifically, the X-ray source may be configured to emit a collimated projection that is substantially linear. The projection line may travel through the object, wherein a portion of the projection is absorbed by the object, to a linear X-ray detector. The linear detector may then convert the detected linear projection into a raw data set. Alternatively, the X-ray source may be configured to emit a collimated projection that is substantially cone shaped. The projection cone may travel through the object, wherein a portion of the projection is absorbed by the object, to a planar X-ray detector. The linear detector may then convert the detected planar projection into a raw data set.

Multiple raw data sets may be collected from the linear or planar detector by changing the positioning of the object with respect to the X-ray source and/or X-ray detector. For example, the object may be placed on a rotary table and rotated. As the object is rotated, multiple raw data sets can be collected as the X-ray source and X-ray detector remain fixed. Specifically, the object may be rotated about 360° with raw data sets produced by the X-ray source and X-ray detector at equal angular increments (e.g., 1440 raw data sets may by collected, with a raw data set collected after the object is rotated about 0.25°). Multiple raw data sets may be collected by causing relative motion of the object with respect to the X-ray source and/or X-ray detector. Thus, the raw data sets may be collected by, for example, rotating an X-ray source and an X-ray detector with respect to the object, rotating an X-ray source with respect to the object and a plurality of X-ray detectors and/or rotating an X-ray detector with respect to the object and a plurality of X-ray sources.

The raw data sets may be reconstructed into an image of greater dimensional complexity than the X-ray detector (i.e., the raw data indicative of absorption or density of the object may be reconstructed into an object image indicative of both the internal and external features of the object). Specifically, raw data collected by a line detector may be utilized to produce a two-dimensional image showing a slice of the object that depicts both internal and external features. A plurality of slices may be combined to produce a full representation of the internal and external features of a three-dimensional object such as, for example, by combining slices collected along a direction orthogonal to the plane of the slices. Raw data collected by a panel detector may be utilized to produce a three-dimensional image of the three-dimensional object. Accordingly, a CT scan can detect and image internal and external features of an object without altering the object. It is to be understood that, while particular variations and principles may be discussed herein with regard to three-dimensional CT or other scanning techniques, any suitable imaging or scanning technique may be used with the present disclosure. It should further be understood that, unless otherwise stated, reference to imaging or to an imaging machine includes imaging machines, MRI, X-ray, CT, and any other applicable scanning or imaging technique or machine.

For illustrative purposes only, the methods described herein can include but are not limited to reconstructing raw data collected from a fixed planar X-ray detector and a fixed X-ray source with a rotating object into a three-dimensional CT data set. An illustrative X-ray CT measurement system is the FlashCT by Hytec Inc. of Los Alamos, N. Mex. Data may be collected with the FlashCT system set on mode 0 resolution (i.e., low resolution) or mode 1 resolution (i.e., high resolution) and an object set from about 1 mm to about 880 mm from the X-ray source with the detector from about 100 mm to about 880 mm from the X-ray source. The X-ray detector may have a resolution of about 1024×768 pixels at low resolution (pixels of about 388 μm) or about 2048×1536 pixels at high resolution (pixels of about 194 μm). The peak X-ray energy may be set from about 65 KVp (kilovolts, peak) to about 100 KVp (kilovolts, peak) with a current from about 250 μA to about 100 μA. The integration time may be from about 33 msec to about 1 sec.

Specifically, when a relatively low amount of penetration is desired, data may be collected with the FlashCT system set on mode 1 resolution and an object set at 700 mm from the X-ray source with the detector 880 mm from the X-ray source. The X-ray detector may have a resolution of about 2048×1536 pixels (pixels of about 194 μm). The peak X-ray energy may be set to about 65 KVp (kilovolts, peak) with a current of about 250 μA with an integration time of about 267 msec. Alternatively, when a relatively high amount of penetration is desired, data may be collected with the FlashCT system set on mode 1 resolution and an object set at 700 mm from the X-ray source with the detector 880 mm from the X-ray source. The X-ray detector may have a resolution of about 2048×1536 pixels (pixels of about 194 μm). The peak X-ray energy may be set to about 80 KVp (kilovolts, peak) with a current of about 200 μA with an integration time of about 267 msec. The FlashCT system may generate raw data with a resolution of about 2048×2048 pixels (pixels of about 154 μm) at capture. About 3200 raw data sets (i.e., projections) from the two-dimensional X-ray detector may be reconstructed into three-dimensional CT data set depicting internal and external features of the scanned object.

As is noted above, any of the absorbent articles, portions or constituents thereof, may be evaluated by imaging techniques to obtain any information of interest, including but not limited to information relating to fluid distribution and containment, fluid flow and transport, product fit, product performance, packaging integrity, product density distribution, how a product fills its packaging, etc. A mannequin may be adapted to display (or wear) an absorbent article. In one example, the mannequin can be placed in an imaging machine for testing purposes (e.g., mounted to a rotating table of a CT system). In another example, the mannequin may be adapted to accommodate fluids or semi-solids that model materials likely to come in contact with the absorbent article. Suitable methods of using the mannequins provided herein are disclosed in commonly assigned, co-pending U.S. Ser. No. 13/161,733, entitled "Methods for Analyzing Absorbent Articles," filed on 16 Jun. 2011.

In some examples of the present disclosure, an absorbent article may be worn by a mannequin so as to obtain information relating to how the absorbent article performs or responds under actual product usage conditions. The mannequin may have various features that enable the absorbent article to be used in a manner that simulates actual usage with respect to the information of interest. For example, where the absorbent article is a diaper, the mannequin may take the form of a frame over which the diaper is positioned, or the mannequin may represent the applicable anatomical geometry of the product's user. Where a mannequin is used, features that simulate actual product usage may include a tube and artificial orifice, or more than one of each, to enable transport of material such as fluid, solid, or semi-solid materials from the inside of the mannequin to the absorbent article from an anatomically correct location, such as in a manner that represents soiling of a diaper by urine from a urethra, fecal matter from a rectum, or both. Specifically, the tube may be dimensioned, constructed, sized, and positioned to simulate a urethra and/or a rectum.

The mannequin may be indicative of an actual person and/or a group of people (i.e., a composite of features from a group or a statistical representation of a group of people). Specifically, as described by U.S. Patent Application No. 2008/0015537 assigned to The Procter & Gamble Company of Cincinnati, Ohio, the pertinent portions of which are incorporated by reference herein, a mannequin may be constructed to correspond to a suitable model infant (e.g., an infant weighing approximately 11.8 kilograms and had proportions typical for a median child in the recommended weight range for PAMPERS size 4 Easy Ups (7.3-15.4 kilograms)). A photographic surface scan of the infant may be taken using a 3 dMD 5 pod torso photographic system (available from 3dMD of Atlanta, Ga.). The surface data from the scan may be enhanced electronically in areas with poor polygon coverage (e.g. perineum creases). A mannequin master may be created using stereolithographic equipment as a hard polymer shell. A molded mannequin may be generated from the shell. In some examples, the mannequin may be indicative of an engineered hypothetical person bearing one or more physical characteristics of interest for measurement. Non-limiting examples of such characteristics may include bodily anomalies which are manifest as the result of disease, mutilation, religious practice, birth defect, piercing, genetics, or trauma.

Referring to FIG. 1, a system 10 for collecting X-ray images is depicted. The system 10 may comprise a photon source 20 and a photon detector 30 configured to generate X-ray data. The photon source 20 may be any type of device configured to generate a beam of photons such as, for example, a collimated beam. The photon detector 30 may be any type of device configured to absorb photons and transform the absorbed photons into a data signal indicative of the absorbed photons. In one example, photons may be generated by the photon source 20. Photons may then be transmitted from the photon source 20 to the photon detector 30 along a transmission path 22. It is noted that, while FIG. 1 depicts a single source and a single detector, the examples described herein may include any number of photon sources and/or any number of photon detectors.

A controller 32 may be communicably coupled, generally indicated by double arrows, to the photon source 20 and/or the photon detector 30 to coordinate the transmission of photons from the photon source 20 and the detection of photon intensity by the photon detector 30. Specifically, the controller 32 may be operable to set the energy level of the photon source 20 and the frame collection rate of the photon detector 30. Moreover, multiple projections may be collected over any suitable period of time such as for generating raw data for CT images. The period of time that is suitable will vary based on the object being imaged, the context in which it is being evaluated, energy level of the photon source 20 and the frame rate of the photon detector 30. For example, projections may be collected by the photon detector at a frame rate of about 3.75 frames per seconds. In examples where four frames are collected per projection (averaged to increase signal to noise ratio), about 3200 projections may be collected for reconstruction into a three-dimensional CT data set which require about 1 hour of data collection. The amount of time required to collect projections may be decreased by reducing the number of frames that are averaged, reducing the number of projections collected, and/or increasing the power level of the photon source. However, image quality may be reduced, i.e., increased noise, increased image artifacts and reduced image resolution.

The system 10 may also comprise a mannequin fixture 40 that is configured to hold or support a test object during the collection of one or more projections. Generally, the mannequin fixture 40 is placed between the photon source 20 and the photon detector 30 and along the transmission path 22 such that an object coupled to the mannequin fixture 40 may absorb photon energy emitted by the photon source. Moreover, the mannequin fixture 40 may be configured to accurately secure a test object in a desired location with respect to the photon source 20 and the photon detector 30. Specifically, a mannequin 100 may be coupled to the mannequin fixture 40 such that the mannequin 100 is positioned in a desired location as relative rotational motion occurs between the mannequin 100 and the photon detector 30. Thus, as is noted above, when the controller 32 causes the photon detector 30 to collect X-ray projections, the mannequin fixture 40 may substantially stabilize (i.e., mitigate undesired motion) the mannequin 100 as the mannequin 100 and/or the photon detector 30 are rotated.

Figure 2:
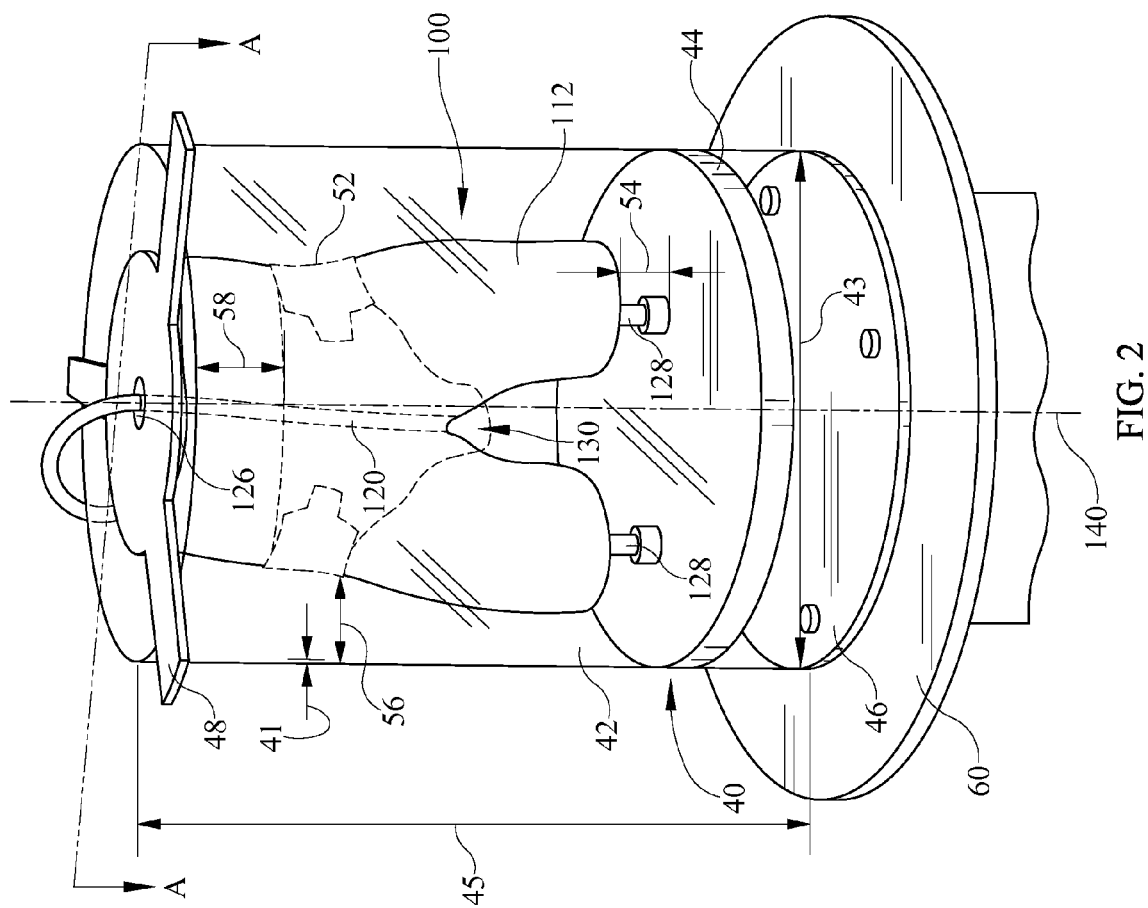
FIG. 2 depicts a mannequin coupled to a mannequin fixture according to one or more examples shown and described herein.

In one example, depicted in FIG. 2, the mannequin fixture 40 may comprise a tube portion 42 that is configured to reduce the introduction of image artifacts and have limited and substantially uniform absorption of photons. The tube portion 42 may be substantially cylindrically shaped with substantially uniform wall thickness 41. The internal diameter 43 and the height 45 of the tube portion 42 may be sized to accommodate the mannequin 100, i.e., internal diameter may be greater than a width of the mannequin and the height may be greater than a height of the mannequin. The tube portion 42 may comprise any type of material with relatively low photon absorption compared to the mannequin 100. Such materials may include plastic, acrylic, and any other substantially radiotranslucent material.

The mannequin fixture 40 may further comprise a first adapter plate 46 configured to be coupled to a rotating table 60 and a second adapter plate 48 configured to be coupled to a mannequin. Each of the first adapter plate 46 and the second adapter plate 48 may be coupled to the tube portion 42 of the mannequin fixture 40 to bound a volume. In one example, the mannequin fixture 40 may comprise a base plate 44 configured to be coupled to the mannequin 100. As depicted in FIG. 2, the base plate 44 may be located between the first adapter plate 46 and the second adapter plate 48 and coupled to the tube portion 42 of the mannequin fixture 40.

Referring back to FIG. 1, the system 10 may comprise a mannequin 100 adapted to simulate actual usage of an absorbent article. In the example depicted in FIGS. 2 and 3, the mannequin 100 may comprise a contoured surface 112 that is formed into a three-dimensional shape that substantially matches the anatomy of a person or a statistical model representing a group of people or a hypothetical person, as described herein.

Figure 3:
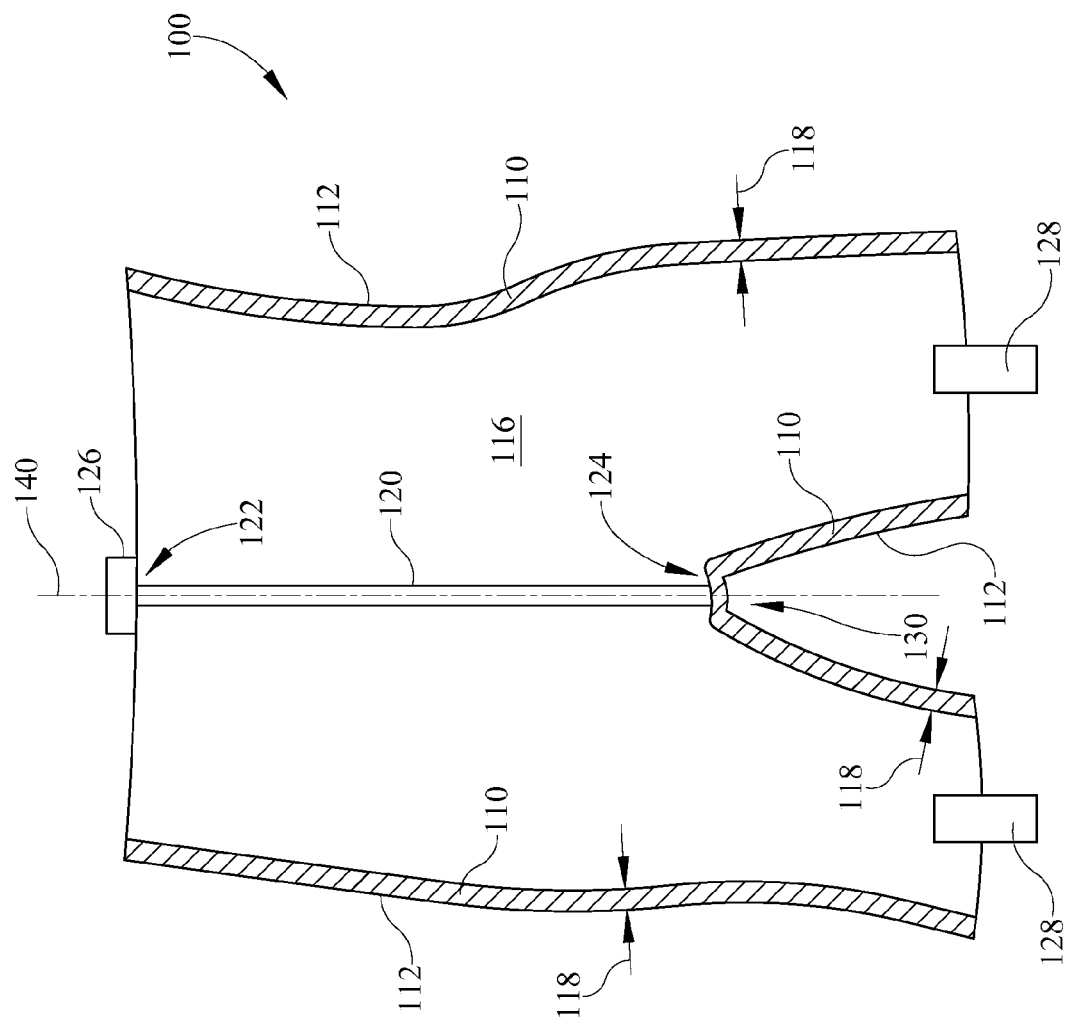
FIG. 3 depicts a cross-sectional view of a mannequin according to one or more examples shown and described herein.

Referring collectively to FIGS. 2 and 3, the mannequin 100 may comprise a contoured surface 112 that is at least partially formed, and is preferably substantially formed, by a skin layer 110. In one example, the contoured surface 112 is the outer portion of the skin layer 110 (i.e., the portion of the skin layer 110 that substantially matches the anatomy of a person). The skin layer 110 may have an average thickness of about 10 mm or less. In one example, the skin layer 110 has an average thickness of about 3 mm. Preferably, the thickness of the skin layer 110 is substantially uniform across the whole skin layer. This advantageously aides in improving the accuracy of the imaging or scanning technique used with the mannequin 100. The skin layer 110 may comprise materials that are substantially rigid and/or flexible. Optionally, the skin layer 110 may be substantially rigid and may have a thickness 118 of less than about 10 mm. For example, the skin layer may comprise a hard plastic material having a thickness of, for example, about 0.5 mm to about 6 mm or about 1 mm to about 3 mm. Suitable hard plastic materials include castable (e.g., spin casting or core cavity molding) hard polyurethane having a Shore hardness (using D scale) of about 60 D to about 80 D, such as of about 62 D to about 67 D, or about 65 D. Specifically, hard polyurethanes such as, for example, RenCast® 6405, RenCast® 6420 (each available from Huntsman Advanced Materials of The Woodlands, Tex.), or WC-765 (available from BJB Enterprises Inc. of Tustin, Calif.) may be utilized according to the skin layers described herein.

In another example, the skin layer 110 may be substantially flexible and may have a thickness of about 5 μm to about 3.175 mm such as, for example, from about 50 μm to about 2 mm, from about 5 μm to about 200 μm, or from about 500 μm to about 3 mm. When the skin layer 110 is flexible, the skin layer 110 may comprise materials having a coefficient of friction and surface energy substantially equivalent to a skin of the person or the statistical model representing a group of people such as a castable, brushable, or sprayable elastomer. Suitable castable, brushable, or sprayable elastomers may comprise polyurethanes having a Shore hardness (using OO and A scales) of about 35 OO to about 15 A, such as of about 40 OO to about 95 OO. Specifically, polyurethane such as, for example, SC-89, SC-80, or SkinFlex III (each available from BJB Enterprises Inc. of Tustin, Calif.) or any flexible paint may be utilized according to the skin layers described herein. It is noted that, while the thickness 118 of the skin layer 110 is depicted in FIG. 3 as being substantially uniform, the thickness 118 may vary according to the ranges described hereinabove.

Referring now to FIG. 3, the mannequin 100 may comprise a photon transmissive filler 116 at least partially surrounded by the skin layer 110. The photon transmissive filler 116 may comprise one or more materials provided that the photon transmissive filler 116 has an average specific gravity of about 0.5 g/cc or less, preferably from about 0.01 g/cc to about 0.5 g/cc, more preferably from about 0.01 g/cc to about 0.25 g/cc, even more preferably less than about 0.12 g/cc, such as, for example, less than about 0.1 g/cc, less than about 0.08 g/cc, less than about 0.07 g/cc, or less than about 0.06 g/cc. In one example, the photon transmissive filler 116 comprises a foam having an average specific gravity of about 0.03 g/cc to about 0.1 g/cc or from about 0.04 g/cc to about 0.1 g/cc such as, for example, a low density water-blown polyurethane foam, an open cell foam and/or a closed cell foam. Accordingly, the photon transmissive filler 116 may comprise polyurethane, latex, polystyrene, polypropylene, synthetic rubber (e.g., ethylene propylene diene monomer (EPDM)), neoprene or combinations thereof. Preferably, the photon transmissive filler 116 is of substantially homogeneous composition. This is believed to aide in the accuracy of the imaging or scanning technique used in conjunction with the mannequin. In some examples, the photon transmissive filler 116 comprises substantially one material. In some examples, the photon transmissive filler 116 comprises one or more discrete air pockets.

According to the examples described herein, a mannequin 100 may have a transmittance parameter value that indicates that the mannequin 100 is suitable for generating CT images. The transmittance parameter value may be generated by utilizing the FlashCT described hereinabove. Specifically, the mannequin may be placed between the X-ray source and the detector of the FlashCT system such that the detector is 880 mm from the X-ray source and the mannequin is 575 mm from the X-ray source, with the thickest portion of the mannequin aligned along the transmission path (i.e., a mannequin for evaluating diapers may be aligned such that one thigh faces the X-ray source and one thigh faces the detector). The transmittance parameter value is derived by collecting a single raw data set with the FlashCT system set on mode 1 resolution, peak X-ray energy of 80 KVp (kilovolts, peak) with a current of about 250 μA. Applicants have surprisingly discovered that 80 KVp energy or less is desirable for CT analysis of low density products, e.g. absorbent articles, e.g. diapers.

Figure 4:
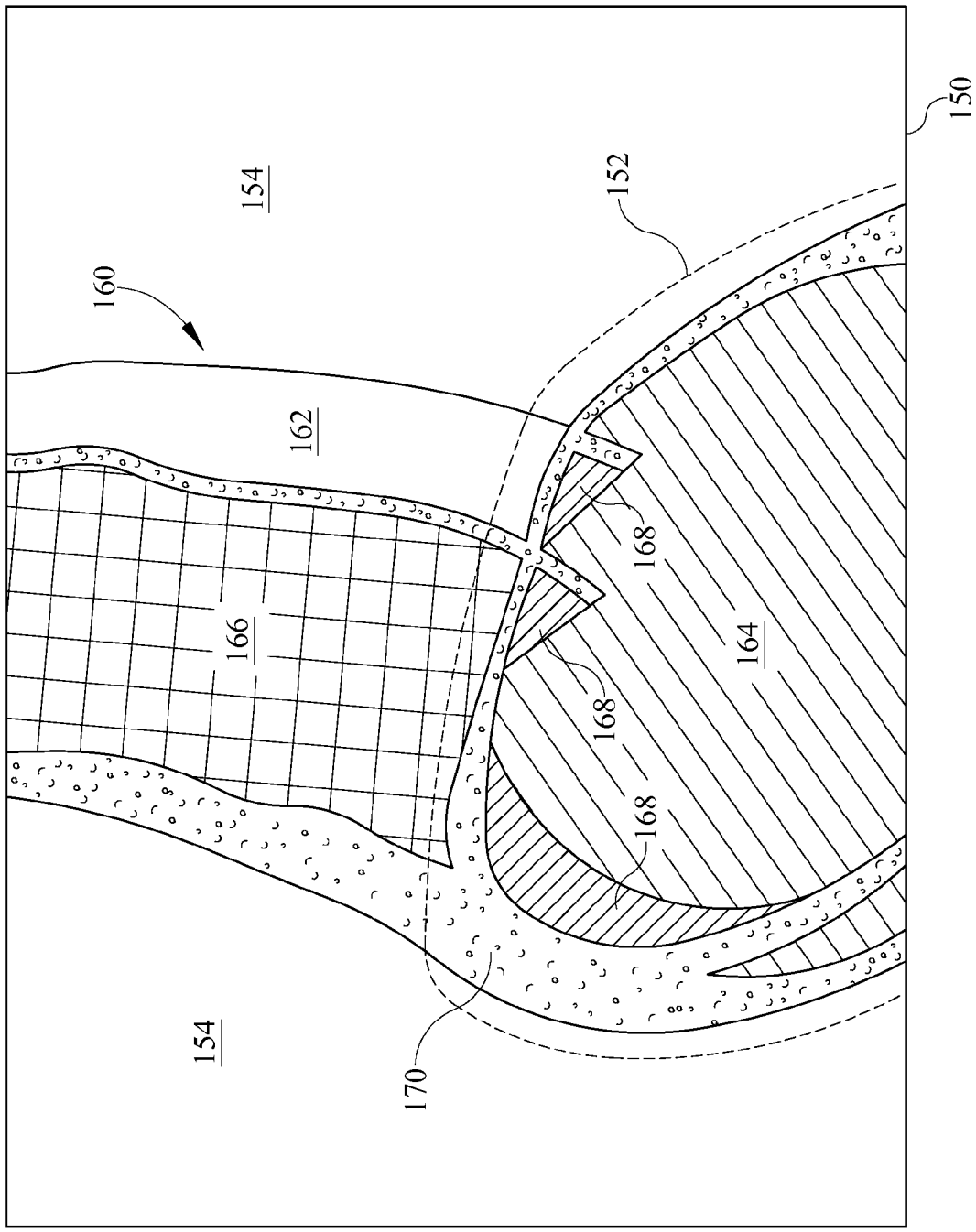
FIG. 4 depicts a test image according to one or more examples shown and described herein.

Referring to FIG. 4, a test image 150 (i.e., raw data set) collected, as described above, is schematically depicted. The test image 150 comprises a mannequin image 160 and a free space image 154, which can be collected with the mannequin upside down as depicted in FIG. 4. The mannequin image 160 corresponds to the image generated by projections from the imaged mannequin. The mannequin image 160 comprises a first value range 162, a second value range 164, a third value range 166, a fourth value range 168 and a fifth value range 170. Pixels within the first value range 162 have higher grey values than pixels within the second value range 164. Pixels within the second value range 164 have higher grey values than pixels within the third value range 166. Pixels within the third value range 166 have higher grey values than pixels within the fourth value range 168. Pixels within the fourth value range 168 have higher grey values than pixels within the fifth value range 170. The transmittance parameter value is calculated for the test image 150 by first taking the average of the grey values of the pixels in the free space image 154 (i.e., areas where photons were not absorbed by the imaged mannequin). The transmittance parameter value is equal to the grey value of a pixel within the mannequin image 160 divided by the average of the grey values of the pixels in the free space image 154 and multiplied by 100%.

Generally, the efficacy of the imaged mannequin is based upon the lowest grey values measured from the portion of the mannequin image 160 within the region of interest 152 (e.g., the portion of the mannequin that is in close contact with the object to be evaluated by the mannequin or the portion of the mannequin that interacts with protons that travel through the object to be evaluated) such as, for example, when the mannequin is for testing a diaper, the perineum region. In the test image 150 depicted in FIG. 4, the pixels within the fifth value range 170 that overlap with the region of interest 152 may have the greatest impact on the efficacy of the imaged mannequin. It is noted that the efficacy of the mannequin is generally measured without the object to be evaluated. Accordingly, it may be necessary to identify the region of interest 152 in a separate test and/or calculation and use known imaging techniques to register the region of interest 152 to the test image.

It has been discovered that when at least a critical portion of the mannequin image 160 within the region of interest 152 has transmittance parameter values greater than a certain percent, the mannequin is suitable for CT imaging. Specifically, when more than about 50% of mannequin image 160 within the region of interest 152 have transmissive parameter values greater than about 10% such as, for example, more than about 60% of the mannequin image 160 within the region of interest 152 has transmissive parameter values greater than about 10%, more than about 80% of the mannequin image 160 within the region of interest 152 has transmissive parameter values greater than about 10%, more than about 90% of the mannequin image 160 within the region of interest 152 has transmissive parameter values greater than about 10% or more than about 95% of the mannequin image 160 within the region of interest 152 has transmissive parameter values greater than about 10%, the imaged mannequin is suitable for CT imaging. Accordingly, the test described herein may be utilized to determine if a mannequin 100 is suitable for evaluating a given absorbent article.

Referring again to FIG. 3, which depicts a cross-sectional view of the mannequin 100 of FIG. 2 taken along plane AA, the mannequin 100 may comprise a fluid flow path 120 for transporting material such as fluid, solid, or semi-solids out of the mannequin 100. The fluid flow path 120 may comprise any material that is substantially radiotranslucent such as plastic and/or rubber. In one example, the fluid flow path 120 may pass through the transmissive filling 116 and terminate at an anatomically accurate location 130 indicative of a urethra or a rectum. Thus, the fluid flow path may be operable to transmit material from the anatomically accurate location during collection of X-ray images. The fluid flow path 120 may have a proximal end 122 and a distal end 124. The distal end 124 of the fluid flow path 120 may be disposed at the anatomically accurate location 130. In another example, the mannequin 100 may comprise a rotary fluid fitting 126 coupled to the proximal end 122 of the fluid flow path 120. When material is introduced through the rotary fluid fitting 126, the fluid flow path 120 may be operable to transmit the material from the proximal end 122 to the distal end 124. The rotary fluid fitting 126 may allow such fluid flow while the mannequin 100 is rotated during the CT imaging process. Thus, the mannequin 100 may wear an absorbent article and simulate in use conditions, as described above.

Referring collectively to FIGS. 1, 2 and 3, the mannequin 100 may comprise fastening members 128 for coupling the mannequin 100 to the mannequin fixture 40. In one example, the fastening members 128 are cast in the photon transmissive filler 116. It is noted that the fastening members may be formed from plastic and may be disposed at the top and/or the bottom on the mannequin 100. Generally, when the mannequin 100 is coupled to the mannequin fixture 40, the mannequin fixture 40 centers the mannequin 100 with respect to the photon source 20 and the photon detector 30. Specifically, the mannequin 100 may comprise an axis of rotation 140 that intersects the mannequin and defines a center for the collection of X-ray images along a substantially circular path. Thus, projections may be collected by the photon source while the mannequin 100 is rotated around the axis of rotation 140, or while the photon source 20 and/or the photon detector 30 are rotated around the axis of rotation 140.

The mannequin 100 can be placed along the transmission path 22 such that photons are transmitted through an imaged portion of the mannequin 100 (i.e., photons are absorbed by the contoured surface 112, the skin layer 110 and/or the photon transmissive filler 116). The mannequin fixture 40 may be configured to improve the quality of images produced by the mannequin 100 by reducing image artifacts generated by interactions between the mannequin fixture 40 and the mannequin 100. In one example, the mannequin 100 may be coupled to the mannequin fixture 40 such that the imaged portion of the contoured surface 112 (i.e., the region of interest 52 of the mannequin such as the perineum region when testing diapers) is spaced at least an artifact distance 56 away (e.g., at least about 2.5 cm) from the mannequin fixture 40.

Referring again to FIG. 2, the fastening members 128 of the mannequin 100 may be coupled to the second adapter plate 48 of the mannequin fixture 40. In order to avoid artifacts, the second adapter plate 48 may be spaced an offset distance 58 from the region of interest 52. Similarly, the fastening members 128 of the mannequin 100 may be coupled to the base plate 44 of the mannequin fixture 40, such that the base plate 44 is spaced an offset distance 54 from the mannequin 100. It is noted that, while FIG. 2 depicts the first adapter plate 46 coupled to a rotating table 60, in further examples of the mannequin fixture 40 the first adapter plate 46 may be omitted and the base plate 44 may be coupled to the rotating table 60.

It should now be understood, that mannequins according to the examples described herein may be configured for use with an X-ray CT system to inspect absorbent articles under realistic conditions. The mannequins generally comprise an interior material with low density such as foam or fluid surrounded by a layer of material shaped to model test subjects. Accordingly, mannequins with a suitable transmittance parameter may include hard plastic skin surrounding air, self-skinning interior foam, foam disposed within a cast skin and foam painted with a skin material.

Although the present disclosure makes reference to particular examples, persons skilled in the art will recognize that changes may be made in form and detail without departing from the spirit and scope of the disclosure. All directional references (e.g., rear, front, left, right, top, bottom) are only used for identification purposes to aid the reader's understanding of the examples of the present invention, and do not create limitations, particularly as to the position, orientation, or use of the invention unless specifically set forth in the claims. It is intended that all matter contained in the above description or shown in the accompanying drawings shall be interpreted as illustrative only and not as limiting. Changes in detail or structure may be made without departing from the spirit of the disclosure as defined in the appended claims.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

All documents cited in the Detailed Description of the Invention are, in relevant part, incorporated herein by reference, however the citation of any document is not construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular examples have been illustrated and described herein, it should be understood that various other changes and modifications may be made without departing from the spirit and scope of the claimed subject matter. Moreover, although various aspects of the claimed subject matter have been described herein, such aspects need not be utilized in combination. It is therefore intended that the appended claims cover all such changes and modifications that are within the scope of the claimed subject matter.

What is claimed is:

1. A mannequin comprising:
   a skin layer comprising a contoured surface, wherein the skin layer has an average thickness of less than or equal to about 10 mm and the contoured surface is formed into a three-dimensional shape that substantially matches an anatomy of a person, a statistical model representing a group of people, or an engineered hypothetical person;
   an axis of rotation intersecting the mannequin, wherein the axis of rotation defines a center for collection of X-ray images along a substantially circular path;
   a photon transmissive filler at least partially surrounded by the skin layer, wherein the photon transmissive filler has an average specific gravity of less than or equal to about 0.5 g/cc; and
   wherein the mannequin represents the lower torso of the engineered hypothetical person.

2. The mannequin of claim 1, wherein the mannequin is suitable for use with at least one imaging or scanning technique selected from Magnetic Resonance Imaging (MRI), X-ray, or computed tomography (CT).

3. The mannequin of claim 2, wherein the mannequin is suitable for use with MRI.

4. The mannequin of claim 2, wherein the mannequin is suitable for use with X-ray.

5. The mannequin of claim 2, wherein the mannequin is suitable for use with CT.

6. The mannequin of claim 1, wherein the three-dimensional shape substantially matches the anatomy of the person.

7. The mannequin of claim 1, wherein the three-dimensional shape substantially matches the anatomy of the statistical model representing the group of people.

8. The mannequin of claim 1, wherein the three-dimensional shape substantially matches the anatomy of the engineered hypothetical person.

9. The mannequin of claim 1, further comprising a fluid flow path passing through the transmissive filling and terminating at an anatomically accurate location indicative of a urethra or a rectum, wherein the fluid flow path is operable to transmit material from the anatomically accurate location during the collection of X-ray images.

10. The mannequin of claim 9, further comprising a rotary fluid fitting coupled to the fluid flow path and disposed along the axis of rotation.

11. The mannequin of claim 1, further comprising plastic fastening members cast in the photon transmissive filler.

12. The mannequin of claim 1, wherein the photon transmissive filler has an average specific gravity from about 0.01 g/cc to about 0.5 g/cc.

13. The mannequin of claim 12, wherein the photon transmissive filler has an average specific gravity from about 0.01 g/cc to about 0.25 g/cc.

14. The mannequin of claim 1, wherein the photon transmissive filler comprises a foam having an average specific gravity of about 0.03 g/cc to about 0.1 g/cc.

15. The mannequin of claim 14, wherein the foam comprises polyurethane, latex, polystyrene, polypropylene, synthetic rubber, or neoprene.

16. The mannequin of claim 1, wherein the photon transmissive filler is substantially homogeneous.

17. The mannequin of claim 1, wherein the photon transmissive filler comprises substantially one material.

18. The mannequin of claim 1, wherein the skin layer comprises an elastomer that forms at least a portion of the contoured surface and the skin layer has a coefficient of friction and surface energy substantially equivalent to a skin of the person or the statistical model, or the engineered hypothetical person.

19. The mannequin of claim 18, wherein the elastomer forms a substantial portion of the contoured surface.

20. The mannequin of claim 18, wherein the elastomer comprises polyurethane.

21. The mannequin of claim 1, wherein the skin layer comprises polyurethane having a Shore hardness from about 60 D to about 85 D.

22. The mannequin of claim 21, wherein the skin layer has a thickness of less than or equal to about 6 mm.

23. The mannequin of claim 1, wherein the skin layer comprises polyurethane having a Shore hardness from about 35 OO to about 15 A.

24. The mannequin of claim 23, wherein the skin layer has the average thickness of about 5 μm to about 3.175 mm.

25. The mannequin of claim 1, wherein the mannequin has a region of interest, and more than about 50% of a mannequin image within the region of interest of a test image of the mannequin has a transmissive parameter value greater than about 10%.

26. The mannequin of claim 1, wherein the skin layer has the average thickness less than or equal to about 5 μm.

27. The mannequin of claim 1, wherein the skin layer has the average thickness of about 3 mm.

28. A mannequin comprising:
   a contoured surface formed into a three-dimensional shape, wherein the three-dimensional shape matches an anatomy of a person, a statistical model representing a group of people, or an engineered hypothetical person;
   a photon transmissive filler at least partially surrounded by the contoured surface;
   more than about 50% of a mannequin image within a region of interest of a test image of the mannequin has a transmissive parameter value greater than about 10%;
   wherein the mannequin represents the lower torso of the engineered hypothetical person; and
   wherein the mannequin further comprises a first adapter plate configured to be coupled to a rotating table and a second adapter plate configured to be coupled to the mannequin.

29. The mannequin of claim 28, wherein the three-dimensional shape substantially matches the anatomy of the person.

30. The mannequin of claim 28, wherein the three-dimensional shape substantially matches the anatomy of the statistical model representing the group of people.

31. The mannequin of claim 28, wherein the three-dimensional shape substantially matches the anatomy of the engineered hypothetical person.

32. The mannequin of claim 28, wherein the photon transmissive filler has an average specific gravity of about 0.03 g/cc to about 0.1 g/cc.

33. The mannequin of claim 32, wherein the photon transmissive filler comprises polyurethane, latex, polystyrene, polypropylene, synthetic rubber, or neoprene.

34. The mannequin of claim 28, wherein the contoured surface is at least partially formed by a skin layer comprising polyurethane.

35. The mannequin of claim 34, wherein the contoured surface is substantially formed by the skin layer comprising the polyurethane.

36. The mannequin of claim 34, wherein the skin layer has a thickness of about 5 μm to about 3.175 mm.

37. The mannequin of claim 36, wherein the skin layer has a Shore hardness from about 35 OO to about 15 A.

38. The mannequin of claim 34, wherein the skin layer has a thickness less than or equal to about 10 mm.

39. The mannequin of claim 38, wherein the skin layer has a shore hardness from about 60 D to about 85 D.

40. The mannequin of claim 28, further comprising:
a fluid flow path having a proximal end and a distal end, wherein the distal end of the fluid flow path is disposed at an anatomically accurate location indicative of a urethra of the person or the statistical model or the engineered hypothetical person, and the fluid flow path passes through the photon transmissive filling; and
a rotary fluid fitting coupled to the proximal end of the fluid flow path, wherein when fluid is introduced through the rotary fluid fitting, the fluid flow path is operable to transmit the fluid from the distal end.

41. A system for collecting X-ray images comprising a photon source, a photon detector, a mannequin, a mannequin fixture, and a controller, wherein:
photons are transmitted from the photon source to the photon detector along a transmission path;
the mannequin comprises a contoured surface, wherein the contoured surface is formed into a three-dimensional shape that substantially matches an anatomy of a person, a statistical model representing a group of people, or an engineered hypothetical person;
the mannequin is placed along the transmission path wherein the photons are transmitted through an imaged portion of the contoured surface;
the mannequin fixture is coupled to the mannequin wherein the imaged portion of the contoured surface is spaced at least an artifact distance away from the mannequin fixture;
the controller causes the photon detector to collect X-ray projections as relative rotational motion occurs between the mannequin and the photon detector; and
wherein the mannequin represents the lower torso of the engineered hypothetical person.

42. The system of claim 41, wherein more than about 50% of a mannequin image within a region of interest of a test image of the mannequin has a transmissive parameter value greater than about 10%.

43. The system of claim 41, wherein;
the mannequin fixture comprises a tube portion; and
the mannequin fixture is placed along the transmission path such that the photons are transmitted through the tube portion of the mannequin fixture.

44. The system of claim 43, wherein the tube portion of the mannequin fixture comprises acrylic.

45. The system of claim 41, wherein:
the mannequin comprises a photon transmissive filler comprising a foam having an average specific gravity of about 0.04 g/cc to about 0.1 g/cc and a skin layer comprising a an elastomer;
the photon transmissive filler is at least partially surrounded by the skin layer; and
the skin layer forms at least a portion of the contoured surface.

46. The system of claim 45, wherein the photon transmissive filler is substantially surrounded by the skin layer.

47. The system of claim 45, wherein the skin layer forms a substantial portion of the contoured surface.

48. The system of claim 45, wherein the skin layer comprises polyurethane having a Shore hardness from about 60 D to about 85 D.

49. The system of claim 45, wherein the skin layer comprises polyurethane having a Shore hardness from about 35 OO to about 15 A.

50. The system of claim 41, wherein the artifact distance is at least about 2.5 cm.

* * * * *